(12) United States Patent
Lubock et al.

(10) Patent No.: US 7,955,246 B2
(45) Date of Patent: Jun. 7, 2011

(54) TEMPORARY CATHETER FOR BIOPSY SITE TISSUE FIXATION

(75) Inventors: Paul Lubock, Laguna Niguel, CA (US); Michael L. Jones, San Clemente, CA (US)

(73) Assignee: Senorx, Inc., Irvine, CA (US)

(*) Notice: Subject to any disclaimer, the term of this patent is extended or adjusted under 35 U.S.C. 154(b) by 852 days.

(21) Appl. No.: 11/980,307

(22) Filed: Oct. 30, 2007

(65) Prior Publication Data

US 2008/0071212 A1 Mar. 20, 2008

Related U.S. Application Data

(60) Division of application No. 11/357,274, filed on Feb. 17, 2006, which is a continuation-in-part of application No. 11/105,856, filed on Apr. 14, 2005, now Pat. No. 7,214,178, which is a continuation of application No. 10/849,410, filed on May 19, 2004, now Pat. No. 6,955,641, which is a continuation of application No. 10/290,002, filed on Nov. 6, 2002, now Pat. No. 6,923,754.

(51) Int. Cl.
*A61N 5/00* (2006.01)

(52) U.S. Cl. .......................................................... 600/3
(58) Field of Classification Search .................. 600/1–8; 604/19, 20
See application file for complete search history.

(56) References Cited

U.S. PATENT DOCUMENTS

| | | | |
|---|---|---|---|
| 5,106,360 A | 4/1992 | Ishiwara et al. |
| 5,167,622 A | 12/1992 | Muto |
| 5,342,305 A | 8/1994 | Shonk |
| 5,417,687 A | 5/1995 | Nardella et al. |
| 5,611,767 A | 3/1997 | Williams |
| 5,662,580 A | 9/1997 | Bradshaw et al. |
| 5,863,285 A | 1/1999 | Coletti |

(Continued)

FOREIGN PATENT DOCUMENTS

EP 0 536 440 4/1993

(Continued)

OTHER PUBLICATIONS

Patent Abstracts of Japan, vol. 2000, No. 22, Mar. 9, 2001 and JP 2001 120561, May 8, 2001.

(Continued)

*Primary Examiner* — Charles A Marmor, II
*Assistant Examiner* — Christine D Hopkins

(57) ABSTRACT

Devices and methods are provided for temporarily maintaining access to a body cavity in a targeted tissue region within a patient's body. One embodiment of the catheter device includes an elongated shaft having a proximal shaft section which is flexible enough to be folded or coiled into a configuration for deployment within the patient. An alternate embodiment includes a catheter device having one or more detachable proximal shaft sections and having at least one one-way valve to restrict fluid flow of inflation fluid to flow to the balloon. After deployment of the catheter device completely within the patient, the opening through which the catheter device is deployed is closed, e.g. by sutures, adhesives and the like to minimize infection at the site. Within a few days or weeks after the tissue has been evaluated for cancer, the temporary catheter device may be removed from the patient. If cancer or pre-cancer cells are found in the specimen removed from the cavity, then a radiation balloon catheter or other irradiation device can be inserted into the patient to irradiate tissue surrounding the biopsy cavity to ensure that cancer cells within the tissue surrounding the cavity are killed.

7 Claims, 4 Drawing Sheets

U.S. PATENT DOCUMENTS

| | | | |
|---|---|---|---|
| 5,913,813 A | 6/1999 | Williams et al. | |
| 5,919,473 A * | 7/1999 | Elkhoury | 424/422 |
| 5,931,774 A | 8/1999 | Williams et al. | |
| 6,022,308 A | 2/2000 | Williams | |
| 6,083,148 A | 7/2000 | Williams | |
| 6,413,204 B1 | 7/2002 | Winkler et al. | |
| 6,458,069 B1 | 10/2002 | Tam et al. | |
| 6,482,142 B1 | 11/2002 | Winkler et al. | |
| 6,673,006 B2 | 1/2004 | Winkler | |
| 2001/0049464 A1 | 12/2001 | Ganz | |
| 2002/0045893 A1 | 4/2002 | Lane et al. | |
| 2002/0095114 A1 | 7/2002 | Palasis | |
| 2002/0177804 A1 | 11/2002 | Saab | |
| 2004/0116767 A1 | 6/2004 | Lebovic et al. | |
| 2005/0240073 A1 | 10/2005 | Apffelstaedt et al. | |

FOREIGN PATENT DOCUMENTS

| | | |
|---|---|---|
| WO | WO 02/09599 | 2/2002 |
| WO | WO 02/069862 | 9/2002 |

OTHER PUBLICATIONS

Patent Abstracts of Japan, vol. 1998, No. 10, Aug. 31, 1998, and JP 10 137250, May 26, 1998.

* cited by examiner

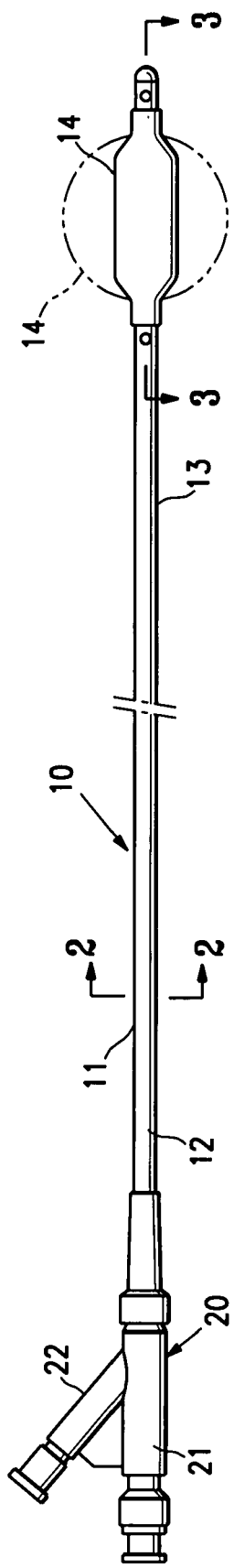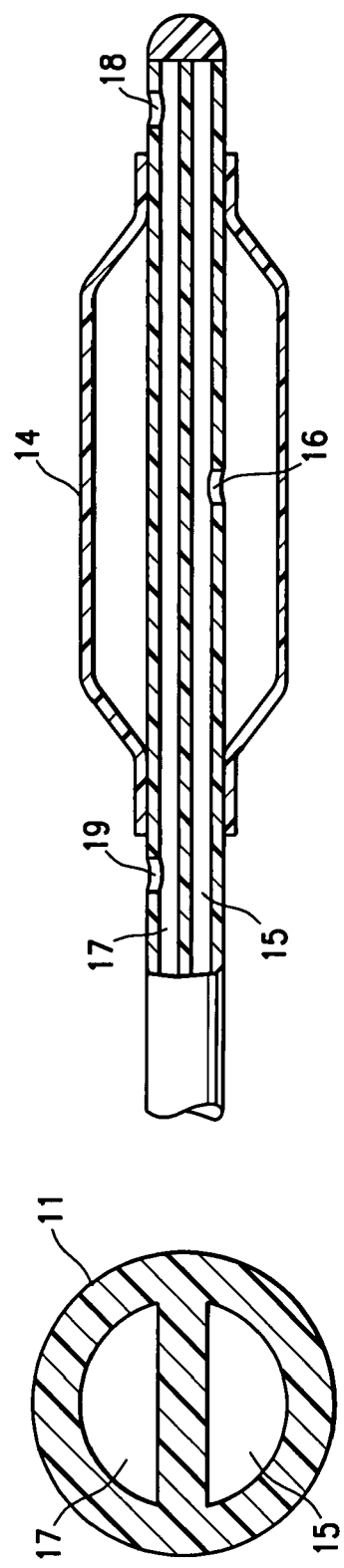
FIG. 1
FIG. 2
FIG. 3

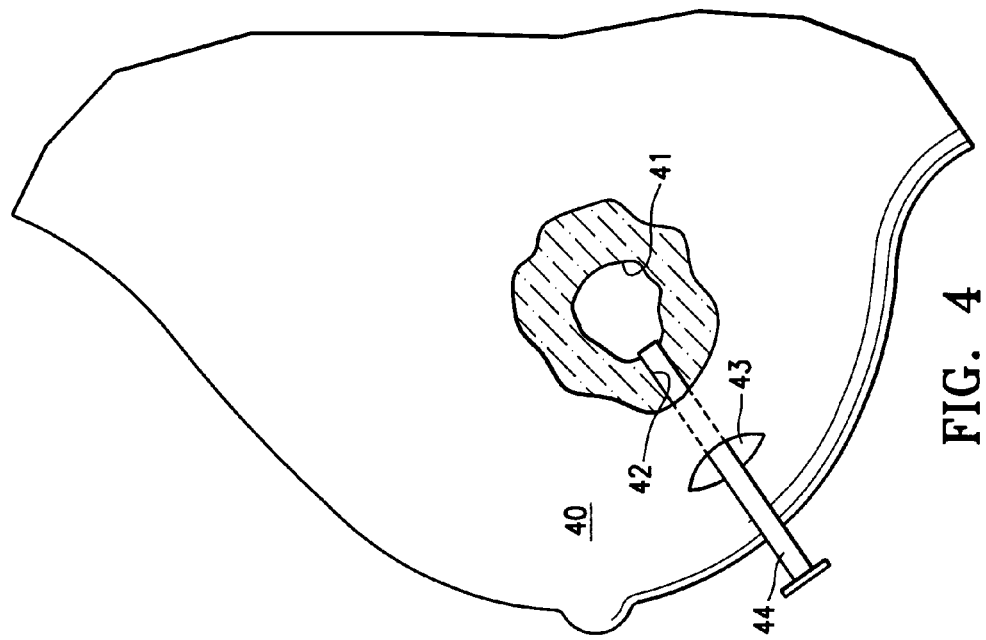
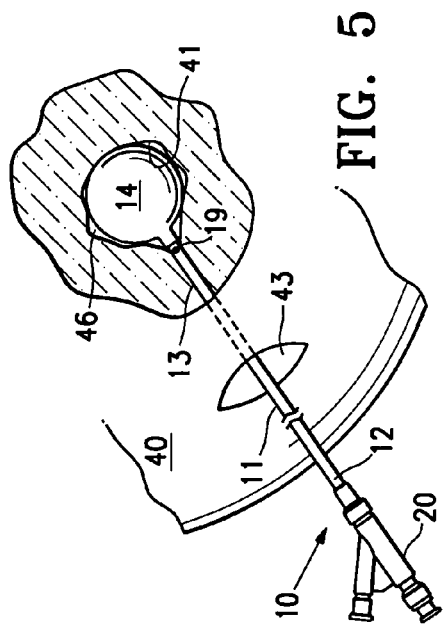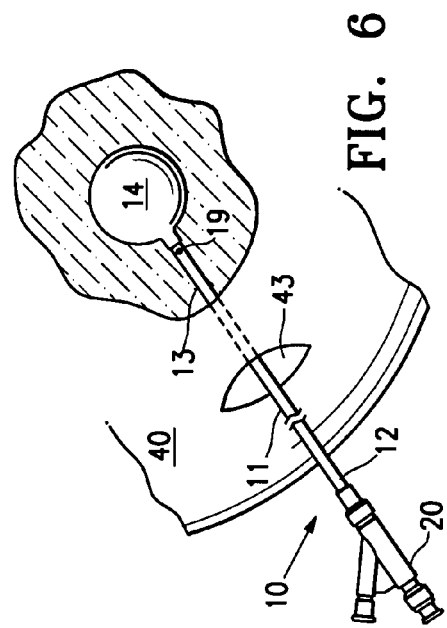

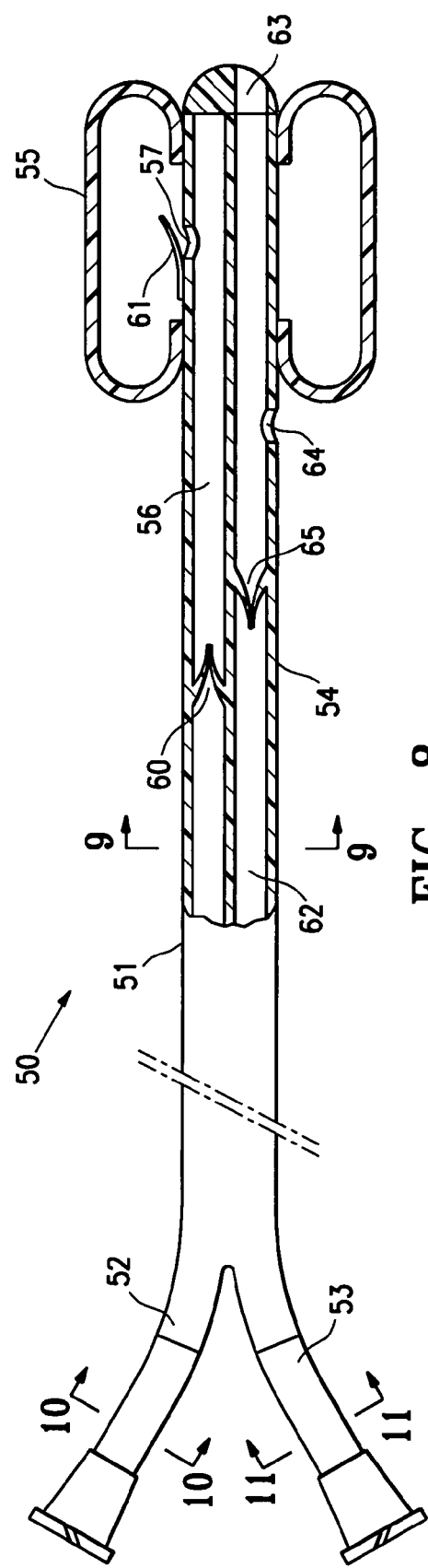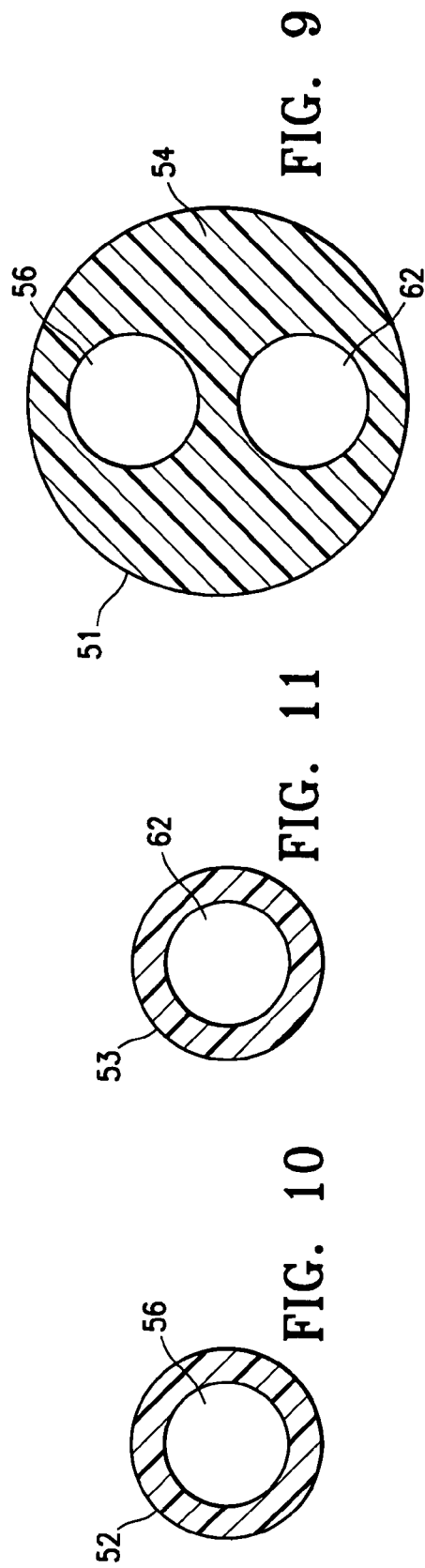

TEMPORARY CATHETER FOR BIOPSY SITE TISSUE FIXATION

RELATED APPLICATIONS

This application is a divisional of application Ser. No. 11/357,274, filed Feb. 17, 2006, which is a continuation-in-part of application Ser. No. 11/105,856 filed Apr. 14, 2005 now U.S. Pat. No. 7,214,178 which is a continuation of application Ser. No. 10/849,410 filed May 19, 2004, now U.S. Pat. No. 6,955,641 which is a continuation of application Ser. No. 10/290,002 filed Nov. 6, 2002, now U.S. Pat. No. 6,923,754. All of these applications are incorporated herein in their entireties by reference and from which priority is claimed.

FIELD OF THE INVENTION

This invention generally relates to medical treatment devices and methods of using such devices. In particular, the invention is directed to devices and methods for temporarily maintaining access to a cavity in a targeted tissue region, such as a biopsy site from which cancerous, pre-cancerous or other tissue has been removed, to provide subsequent treatments to the tissue surrounding the cavity.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example U.S. Pat. No. 6,923,754 to Lubock and U.S. patent application Ser. No. 10/849,410 to Lubock, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

The Lubock patent and patent application, above, describe implantable devices for treating tissue surrounding a cavity left by surgical removal of cancerous or other tissue that includes a cavity filling member such as an inflatable balloon constructed for placement in the cavity. The Lubock devices develop a vacuum within the biopsy cavity that is effective to draw surrounding tissue close to the surface of a treatment assembly so as to conform the tissue lining the cavity to the surface of the balloon. Such devices may be used to apply one or more of radiation therapy, chemotherapy, and thermal therapy to the tissue surrounding the cavity from which the tissue was removed. The balloon may be filled with a treatment fluid delivered via a conduit from a receptacle, syringe, or other means, or may receive a solid radiation source placed within the balloon.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

Long term deployment of the catheter within the biopsy site may be necessary, e.g. for a few days to a few weeks to maintain access to the biopsy cavity while the biopsy sample is analyzed and it is determined whether or not irradiation of the cavity is necessary. The irradiation is not always necessary for a body cavity formed after removal of tissue. When irradiation is not needed the catheters are removed and disposed of. When in place within the patient, the proximal ends of the prior art catheters extend out of the patient providing direct access for infections to reach the biopsy site.

The prior catheters are expensive and a catheter used only to hold the shape of the biopsy cavity is disposed of afterwards. Thus there is need in the art for less expensive devices which are temporary and capable of maintaining access to the biopsy device with reduced risk of infection.

SUMMARY OF THE INVENTION

The invention is directed to methods and devices for temporary subcutaneous deployment while at least partially filling a body cavity in a targeted tissue region within a patient's body, such as a cavity formed by the removal of tissue from a patient. The catheter device embodying features of the invention has distal shaft section with a cavity filling member such as an inflatable member (e.g. balloon) and the proximal shaft portion of the device is configured to be deployed subcutaneously so that no direct access is provided to the intracorporeal cavity for pathogens.

One embodiment of a catheter device having features of the invention has a proximal shaft section that is flexible enough to be folded, e.g. folded over upon itself, or coiled and placed within a subcutaneous region through an opening in the patient's skin. After deployment of the proximal shaft section of the catheter device, the opening in the patient's skin is closed or sealed, e.g. by sutures, staples or clips adhesives and the like.

In another embodiment of a catheter device having features of the invention has a detachable proximal shaft section or sections to allow the distal shaft section of the catheter device to remain within the patient and sealed therein by closing the access opening in the patient's skin, Additionally, the catheter device and method of using the device may include application of a vacuum within the body cavity that is effective to draw tissue surrounding the body cavity towards the surface of the cavity filling member of the catheter device, which is placed within the body cavity.

A catheter device embodying features of the invention may also include an anti-bacterial agent on or incorporated within a surface of the device to further prevent infection. The catheter device is preferably configured to be deployed within the patient for a period of time from a few days to a few weeks.

The flexible proximal shaft section may be formed of suitable compliant polymers such as polyolefins (e.g. polyethylene and polypropylene), polyurethanes, polyesters, polyvinylchloride, polystyrene, thermoplastic polymers such as C-Flex® (Consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g., SILASTIC®, Dow Corning, Midland, Mich.).

Body cavities, particularly cavities from which tissue has been removed (e.g. for biopsy) are typically not uniform in size or regular in shape. The catheter devices and systems and methods of using such devices or systems having features of the invention utilize suction to draw tissue surrounding the body cavity against the surface of the cavity filling member on the distal shaft section of the catheter device within a body cavity to ensure good contact therebetween.

BRIEF DESCRIPTION OF THE DRAWINGS

FIG. 1 is a partial elevational view of a catheter device embodying features of the invention which has a balloon configured to temporarily maintain the shape of a cavity in a patient's body tissue.

FIG. 2 is a transverse cross-sectional view of the catheter device shown in FIG. 1 taken along line 2-2.

FIG. 3 is an enlarged longitudinal cross section of the distal shaft section of the catheter device shown in FIG. 1 taken along the line 3-3.

FIG. 4 is an elevational view, partially in section, of a patient's breast after removal of a tissue specimen therefrom.

FIG. 5 is a partial elevational view, partially in section, of a patient's breast device with the catheter shown in FIG. 1 deployed within the patient and the cavity filling balloon inflated within the cavity.

FIG. 6 is a partial elevational view, partially in section, of a patient's breast with the catheter device shown in FIG. 1 deployed within the patient with the cavity filling balloon inflated within the cavity and after the application of a vacuum within the cavity to pull the cavity lining into contact with the inflated cavity filling balloon.

FIG. 8 is an elevational view of a temporary catheter having features of the invention having a detachable proximal portion or portions which can be removed after the distal shaft section has been deployed within the patient.

FIG. 9 is a transverse cross-sectional view of the catheter device shown in FIG. 8, taken along the lines 9-9.

FIG. 10 is a transverse cross-sectional view of the catheter device shown in FIG. 8, taken along the lines 10-10.

FIG. 11 is a transverse cross-sectional view of the catheter device shown in FIG. 8, taken along the lines 11-11.

DETAILED DESCRIPTION OF EMBODIMENTS

Figure 7:
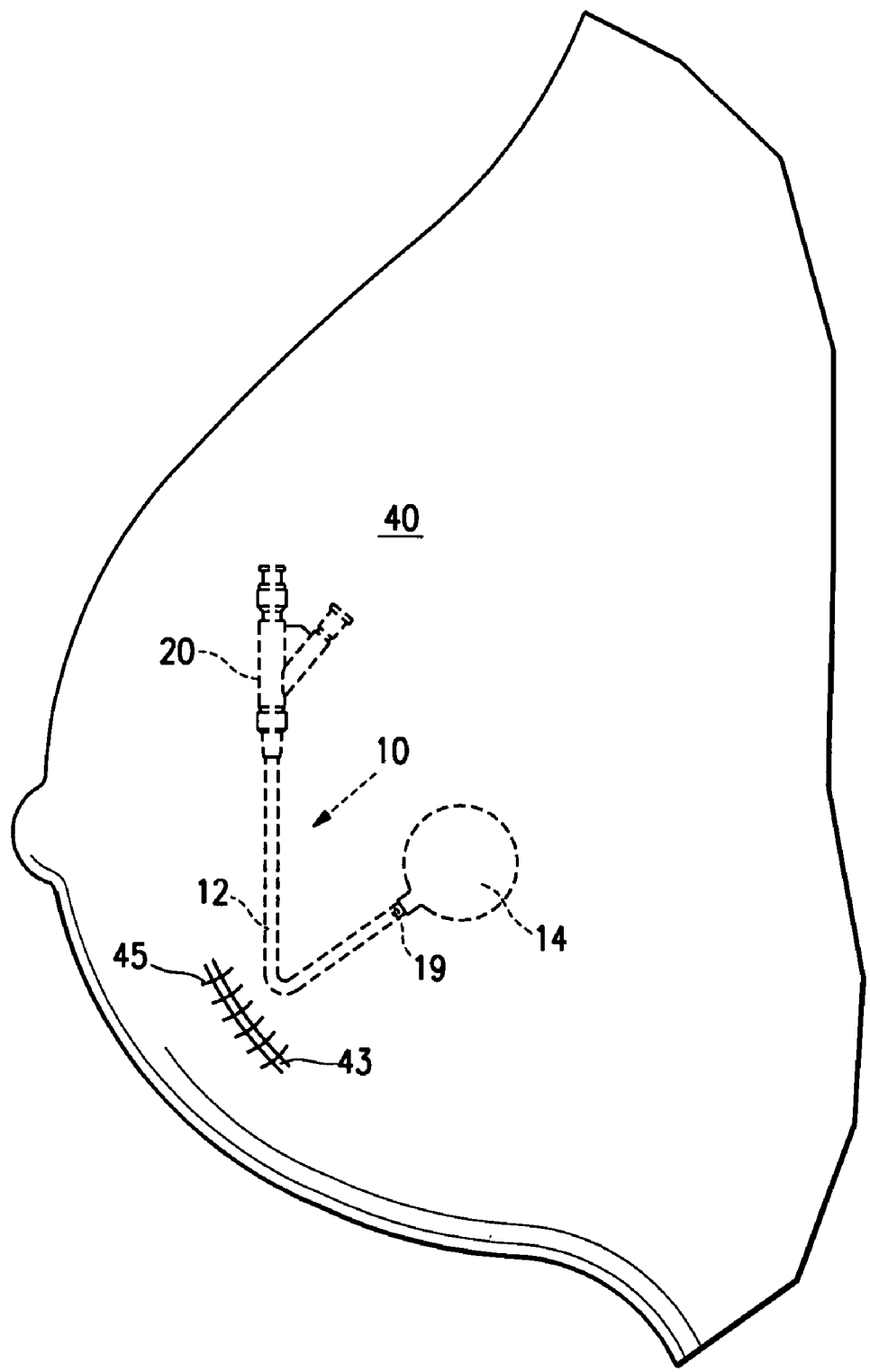
FIG. 7 is an elevational view of a patient's breast with the catheter shown in FIG. 1 completely deployed within the patient and the surgical opening closed.

The present invention is directed to catheter devices and methods of using such devices for temporarily maintaining access to an intracorporeal cavity in a targeted tissue region within in a patient's body, such as a biopsy site or a cavity left after removal of a tissue specimen. The catheter device embodying features of the invention has an elongated shaft with a proximal shaft portion that is either detachable or foldable or coilable to facilitate deployment of the proximal end of the catheter within the tissue surrounding the biopsy site. After tissue has been removed from the targeted tissue region, the cavity filling member on the distal end of the catheter is inserted through an opening in the patient's skin and advanced through a passageway in the patient to the body cavity where the cavity filling member is deployed. The proximal shaft section of the catheter is folded or coiled and placed in a subcutaneous location and the opening in the patient's skin is closed or otherwise sealed, e.g. by sutures, staples, clips, adhesive or the like. A vacuum may be applied to cavity to enhance contact between the cavity filling member and the tissue defining the cavity before the opening in the patient's skin in closed or sealed.

FIGS. 1-3 illustrate a catheter device 10 embodying features of the invention which has an elongated shaft 11, a flexible proximal shaft section 12, a distal shaft section 13 and a cavity filling inflatable balloon 14 on the distal shaft section. As shown in FIGS. 2 and 3, the elongated shaft 11 has an inflation lumen 15 extending from the proximal end of the shaft 11 to a discharge port 16 to discharge inflation fluid within the interior of the balloon 14. The elongated shaft 11 also has a vacuum lumen 17 which extends from the proximal end of shaft 11 to a vacuum port 18 located distal to the balloon 14 and a vacuum port 19 proximal to the balloon 14. Alternatively, individual vacuum lumens may be provided for each vacuum port. Passage of inflation fluid through inflation lumen 15 and discharge port 16 is effective to inflate the balloon 14. Inflation fluid may be a gas or a liquid, and is typically inert. Suitable gases may be air, nitrogen or carbon dioxide. Suitable fluids include water, saline, mineral oil and contrast media with radiopaque material. The balloon in an inflated configuration is shown in phantom in FIG. 1.

Vacuum applied through the one or more vacuum ports 18 and 19 to the body cavity is effective to urge tissue surrounding the cavity into contact with at least a portion of the surface of the outer balloon 14.

The catheter device 10 has a two-arm adapter 20 on the proximal end of the elongated shaft 11. One arm 21 has an inner lumen (not shown) that is in fluid communication with the inflation lumen 15 and the other arm 22 has an inner lumen (not shown) that is in fluid communication with the vacuum lumen 17.

FIG. 4 illustrates a patient's breast 40 which has had a tissue specimen removed, leaving a biopsy cavity 41. An accessing passageway 42 extends from an opening 43 made in the patient's skin to the cavity 41. A cannula 44 remains disposed in the passageway 42 after the biopsy device has been removed.

FIG. 5 illustrates the catheter device shown in FIG. 1 disposed within the patient with the cavity filling balloon 13 inflated within the cavity 41 in the patient's breast FIG. 6 illustrates the body cavity 41 after a vacuum is applied to the cavity so as to conform the tissue of the body cavity 41 to the exterior of the balloon 14.

After the balloon 14 is inflated within the body cavity 41, the flexible proximal shaft section 12 with attached adapter 20 is folded over (or coiled) within the patient's breast 40 and the opening 43 sutured closed with sutures 45. Alternatively, the opening can be closed with a suitable adhesive. A suitable adhesive may also be employed to seal the opening after closure with sutures.

The flexible proximal shaft section 12 can be made flexible enough to be deployed folded or coiled within the patient's breast by thinning the wall of the section or making the wall of a compliant or semi-compliant polymeric material which provides the desired flexibility. Suitable polymeric materials include polyurethane, silicone, C-Flex and Kraton. The proximal shaft section 12 should not have a spring back which would cause discomfort or pain to the patient. The adapter 20 is also preferably formed of flexible materials to facilitate deployment and to minimize pain and discomfort.

The exterior surfaces of the shaft 11 and the balloon 14 are preferably provided with an anti-microbial agent or biocide which retards or prevents pathogen growth within the cavity 41 or the passageway 42. Suitable anti-microbial agents or biocides include silver ions in a hydrophilic carrier, silver ions implanted into the surface of the shaft by ion beam deposition, an antiseptic or disinfectant such as chlorhesqdiene, benzyl chloride. Suitable anti-microbial coatings are provided by Spire, AST, Algon, Surfacine, Ion Fusion and Bacterin International. Other treatment agents such as chemotherapeutic agents may be coated onto or incorporated within the surface of the catheter shaft 11 or balloon 14.

The catheter device 10 which embodies features of the invention is designed to remain within the patient for a few days to several weeks. For example, the catheter device 10 is deployed within the patient's breast after a biopsy specimen has been removed leaving a cavity 41. The catheter device 10 prevents tissue growth within the cavity 41 and the passageway 42. Evaluation of the tissue specimen after removal will determine whether cancer or pre-cancer cells are present or not. If no cancer or pre-cancer cells are found in the specimen, the catheter device may be removed from the patient, the opening re-closed and the catheter device discarded. If cancer cells are found, a radiation balloon catheter such as described in U.S. Pat. No. 6,923,754 to Lubock and U.S. patent application Ser. No. 10/849,410 to Lubock may be utilized to provide radiation treatment to the tissue surrounding the cavity after the temporary catheter device is removed from the patient. The radiation balloon catheter may be advanced through the passageway 42 until the balloon on the catheter is deployed within the cavity 41. The radiation balloon is inflated in a conventional manner so that a uniform dose of radiation is provided to the tissue lining the cavity.

Although a cavity 41 is typically an artificial cavity remaining after removal of tissue at biopsy, surgery, or other medical procedure, a body cavity may be a natural body cavity. For example, devices 10 may be inserted into a bladder for the treatment of bladder cancer. Application of suction is effective to enhance contact with a device 12 in such an example as well. Such enhanced contact may be effective to improve the delivery of radiation or other treatment, and may be effective to avoid "hot spots" (tissue regions receiving more radiation than is received by neighboring tissue regions) and is one of the important advantages provided by the present invention.

Vacuum applied to intermediate space 45 effects good contact between tissue surrounding body cavity 41 and the wall of the balloon 14.

FIGS. 8-11 illustrate a catheter device 50 embodying features of the invention which has an elongated shaft 51, detachable proximal shaft sections 52 and 53, a distal shaft section 54 and a cavity filling inflatable balloon 55 on the distal shaft section. The elongated shaft 51 has an inflation lumen 56 extending from the proximal end of the detachable proximal shaft section 52 to a discharge port 57 in fluid communication with the interior of balloon 55 to discharge inflation fluid therein to inflate the balloon 55. A one-way valve element 60 is disposed within the inflation lumen 56 to allow passage of inflation fluid to the interior of the balloon 55 but prevent discharge of the inflation fluid in the reverse direction. Alternatively or additionally, a one-way valve 61 may also be employed at the discharge port 57 for the same purpose.

The elongated shaft 51 may also has a vacuum lumen 62 which extends from the proximal end of detachable proximal shaft section 53 to a vacuum port 63 located distal to the balloon 55 and a vacuum port 64 proximal to the balloon. A one-way valve 65 may be provided within the vacuum lumen 62 to maintain the vacuum which is developed within the body cavity. While only one vacuum lumen 62 is shown in communication with the vacuum ports 63 and 64, separate vacuum lumens may be provided for each of the vacuum ports.

The one way valve elements 60 and 65 provided within the inflation and vacuum lumens 56 and 62 respectively may be reed or duckbilled valve elements. The one way valve 61 may be a flapper valve.

The detachable proximal shaft sections 52 and 53 may be connected to the distal shaft section 54 of the catheter device 50 by threaded connections, friction fit connections or other suitable releasable connections. Moreover, while separate detachable proximal shaft sections are shown, they may be combined into a single detachable proximal shaft section.

After a biopsy specimen is removed from the patient, leaving a cavity therein, the catheter device 50 is advanced within the patient until the cavity filling balloon 55 is disposed within the cavity. Inflation fluid is introduced into the interior of the balloon 55 through the inflation lumen 56. The inflation fluid passes through the one-way valve 60 on its way to the balloon interior. Pressure within the lumen distal to the valve 60 and/or the valve structure prevents inflation fluid from passing proximally through the valve. The balloon 55 is inflated to at least partially fill the body cavity within the patient and preferably not to stretch the tissue surrounding the cavity. Vacuum is then pulled through the vacuum ports 64 and 65 to draw the tissue surrounding the cavity towards the balloon 55 to conform the tissue lining to the exterior of the inflated balloon.

Once the balloon 55 is inflated and the vacuum developed to conform the tissue lining to the exterior of the balloon 55, the proximal shaft sections 52 and 53 can be detached from the catheter shaft and the opening in the patient's skin can be closed by suturing, adhesives or other suitable means. The one way valves 60 and/or 61 and 65 minimize or prevent loss of inflation fluid and vacuum.

The portion of the catheter device 50 which remains in the patient can be removed by accessing the proximal portion of the catheter device which remains in the patient by opening the original opening that had been closed or forming a new opening in the patient's skin. The catheter shaft can be severed proximal to the balloon to release the inflation fluid and deflate the balloon to facilitate its withdrawal. If needed, a radiation balloon catheter can be inserted into the patient as previously described to irradiate the tissue lining of the body cavity. If radiation or other treatment is not needed, the opening in the patient's skin may be closed.

While particular forms of the invention have been illustrated and described herein, it will be apparent that various modifications of the invention can be made to the invention. For example, while the various embodiments of the invention have been described herein in terms of a catheter device for treating a biopsy site, it should be apparent that the catheter device and the method of use may be employed elsewhere in the patient's body. Accordingly, it is not intended that the invention be limited to the specific embodiments illustrated.

Terms such as "element", "member", "device", "section", "component", "portion", "means", "step" and words of similar import, when used in the following claims, shall not be construed as invoking the provisions of 35 U.S.C. §112(6) unless the claims expressly use the term "means" followed by a particular function without specific structure or the terms "step" or "steps" followed by a particular function without specific action. All patents and patent applications referred to herein are incorporated by reference in their entirety.

What is claimed is:

1. A method of temporarily filling an intracorporeal site within a patient's body, comprising:
   a. providing a catheter device having an elongated shaft with a flexible proximal shaft section, a distal shaft section and a cavity filling member on the distal shaft section;
   b. forming a passageway from an opening in the patient's body to a desired intracorporeal location;
   c. forming a cavity at the desired intracorporeal location;
   d. inserting the catheter device through the opening and advancing the catheter device within the passageway until the cavity filling member on the distal shaft section is disposed within the cavity, wherein the cavity filling member is an inflatable balloon and the inflatable balloon is inflated after deployment within the cavity;
   e. folding or coiling the flexible proximal shaft section and placing the folded or coiled flexible proximal shaft section within the patient's body;
   f. closing the opening;
   g. deflating the inflated inflatable balloon;
   h. opening the closing or forming a new opening;
   i. removing the catheter device from the patient; and
   j. inserting a radiation balloon catheter having an inflatable balloon on a distal shaft section into the patient through the passageway and inflating the inflatable balloon on the radiation balloon catheter to expand the inflatable balloon within the cavity.

2. The method of claim 1 wherein a vacuum is generated within the body cavity to draw the tissue lining the cavity towards the inflated inflatable balloon of the catheter device to conform the tissue to the inflatable balloon of the catheter device.

3. A method for treating a biopsy site within a patient comprising:
   a. forming a passageway from an opening in an exterior site on the patient to a desired location for a biopsy specimen;
   b. removing a tissue specimen therefrom with a biopsy device leaving a biopsy cavity;
   c. providing a temporary catheter having an elongate shaft, a flexible proximal shaft section configured to be folded or coiled, and a distal shaft section having a cavity filling member thereon;
   d. inserting the cavity filling member on the distal shaft section into the biopsy cavity;
   e. deploying the flexible proximal shaft section in a folded or coiled configuration at an intracorporeal location; and
   f. closing the opening so as to seal the passageway extending therefrom; and
   wherein a vacuum is applied to the biopsy cavity to conform tissue lining the biopsy cavity to the cavity filling member.

4. A method for treating a biopsy site within a patient comprising:
   a. forming a passageway from an opening in an exterior site on the patient to a desired location for a biopsy specimen;
   b. removing a tissue specimen therefrom with a biopsy device leaving a biopsy cavity;
   c. providing a temporary catheter having an elongate shaft, a flexible proximal shaft section configured to be folded or coiled, and a distal shaft section having a cavity filling member thereon;
   d. inserting the cavity filling member on the distal shaft section into the biopsy cavity;
   e. deploying the flexible proximal shaft section in a folded or coiled configuration at an intracorporeal location; and
   f. closing the opening so as to seal the passageway extending therefrom; and
   wherein the temporary catheter is removed from the patient and a radiation treatment catheter is deployed so as to irradiate the biopsy cavity.

5. A method for maintaining access to a body cavity from which tissue has been removed, comprising:
   a. providing a catheter having an elongate shaft, proximal and distal ends, a distal shaft section proximal to the distal end, a flexible proximal shaft section, a cavity filling member on the distal shaft section configured to at least partially fill the body cavity, a vacuum port proximal or distal to the cavity filling member and a vacuum lumen extending to and in fluid communication with the vacuum port;
   b. inserting the catheter through an opening in the patient's skin and advancing the catheter through a passageway within the patient until the cavity filling member on the distal shaft portion of the cavity filling member of the catheter is disposed within the body cavity from which tissue has been removed;
   c. expanding the cavity filling member within the body cavity; and
   d. generating a vacuum within the vacuum lumen to aspirate fluid from the body cavity through the vacuum port and to conform the tissue lining the cavity to the cavity filling member.

6. The method of claim 5 wherein the proximal shaft section is deployed in a folded or coiled configuration within a subcutaneous region of the patient.

7. The method of claim 6 wherein the opening in the patient's skin is closed so as to prevent pathogen access therethrough.

* * * * *